United States Patent [19]

Yang

[11] Patent Number: 6,106,555
[45] Date of Patent: Aug. 22, 2000

[54] METHOD FOR TISSUE FIXATION

[75] Inventor: Jun Yang, Dove Canyon, Calif.

[73] Assignee: AV Healing LLC, Dove Canyon, Calif.

[21] Appl. No.: 09/212,328

[22] Filed: Dec. 15, 1998

[51] Int. Cl.$^7$ .................................. A61F 2/02; A61F 2/00
[52] U.S. Cl. .......................................... 623/11.11; 424/426
[58] Field of Search ........................... 623/11.11; 424/426

[56] References Cited

U.S. PATENT DOCUMENTS

| | | | |
|---|---|---|---|
| 3,485,573 | 12/1969 | Heyden . | |
| 4,082,507 | 4/1978 | Sawyer . | |
| 4,690,973 | 9/1987 | Noishiki et al. . | |
| 4,806,595 | 2/1989 | Noishiki et al. . | |
| 4,883,864 | 11/1989 | Scholz | 530/356 |
| 4,976,733 | 12/1990 | Girardot | 623/11 |
| 5,067,961 | 11/1991 | Kelman et al. . | |
| 5,080,670 | 1/1992 | Imamura et al. . | |
| 5,314,874 | 5/1994 | Miyata et al. . | |
| 5,376,110 | 12/1994 | Tu et al. . | |
| 5,549,666 | 8/1996 | Hata et al. . | |
| 5,591,225 | 1/1997 | Okuda . | |
| 5,674,298 | 10/1997 | Levy et al. . | |
| 5,733,339 | 3/1998 | Girardot et al. . | |
| 6,017,900 | 1/2000 | Falk et al. | 514/54 |
| 6,028,066 | 2/2000 | Unger | 514/180 |

FOREIGN PATENT DOCUMENTS

| | | |
|---|---|---|
| 0212933 | 10/1990 | European Pat. Off. . |
| 0306256 | 3/1994 | European Pat. Off. . |
| WO9401481 | 1/1994 | WIPO . |
| WO9417841 | 8/1994 | WIPO . |

OTHER PUBLICATIONS

Tu, et al., Fixation of Bioprosthetic Tissues With Monofunctional and Multifunctional Polyepoxy Compounds, 1994, pp. 677–684.

An FTIR–ATR Investigation of In Vivo Poly(Ether Urethane) Degradation, Y. Wu et al., 1992. pp. 201–211.

Schubert et al., Oxidative Biodegradation Mechanisms of Biaxially Strained Poly(Etherurethane Urea) Elastomers, 1995, pp. 337–347.

Sutherland et al., Degradation of Biomaterials by Phagocyte–Derived Oxidants, 1993, 2360–2367.

Baier et al., The Relation of the Internal Surface of Crafts to Thrombosis, Chapter 9, pp. 147–163, 1971.

Pol et al., In Vivo Testing of Crosslinked Polyethers. I. Tissue Reactions and Biodegradation, 1996, pp. 307–320, 321–331.

*Primary Examiner*—Michael J. Milano
*Assistant Examiner*—Hieu Phan
*Attorney, Agent, or Firm*—Raymond Sun

[57] ABSTRACT

The present invention provides an epoxy compound that has a hydrocarbon backbone, that is water-soluble, and which does not contain an ether or ester linkage in its backbone. Examples of suitable epoxide agents include mono- or diepoxides that have the following basic formulas:

Monoepoxide:

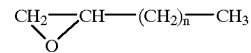

Diepoxide:

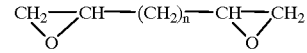

where n=1 to 10.

6 Claims, 2 Drawing Sheets

METHOD FOR TISSUE FIXATION

BACKGROUND OF THE INVENTION

1. Field of the Invention

The present invention relates generally to tissue fixation, and in particular, to an epoxy compound and method for use in tissue fixation.

2. Description of the Prior Art

Biological tissues such as autologous pericardium and homologous aortic valves have been used in various surgical applications because of their good mechanical properties and biocompatibility. Biological tissue-derived, chemically-modified heterologous tissues have been provided as conduits for peripheral or coronary revascularization, patches, ligament substitutes, and prosthetic heart valves. It is well-known that collagen fibers constitute the fundamental structural framework of biological tissues.

The physiochemical and biomechanical properties of collagen matrices are directly related to the structure of the collagen fibrils. The collagen molecules are stabilized in the fibrils by covalent intermolecular crosslinks, which provide the fibrillate matrices with an adequate degree of tensile strength and biostability.

After a prosthesis having heterologous tissue has been implanted in a living host environment, the biological tissue will be subject to a host response, which includes both cellular and enzymatic attack. Previous studies have shown that implanted heterologous collagenous tissues provoke a cellular response which leads to physical invasion of the implanted prosthesis by phacocytes (polymorphonuclear leukocytes, macrophages) and fibroblasts. Phagocytes are known to be able to secrete collagenase and other proteases and oxygen free radicals. Heterologous biological tissues can be readily degraded by such proteolytic enzymes, and/or through an oxidation process, significantly reducing the strength and life span of the collagen fibrils. To achieve long-term stability, bioprostheses derived from heterologous tissues have to be chemically modified to increase their resistance to enzymatic degradation before they can be implanted into a human being for long term use. These chemical modifications include:

(1) Crosslinking to stabilize the collagen matrix, such as enhancing the molecular interaction between collagen fibrils, elastin and other proteins; increasing tissue fatigue limit under stress; and maintaining the tissue integrity and preventing inflammatory cell infiltration;

(2) Modification of collagenous tissue to minimize the immunogenicity: heterologous tissue needs to be modified to reduce the immunogenicity so that systemic and local adverse effects (e.g., chronic inflammation or rejection) will be minimized;

(3) Modification to minimize enzymatic attack: chemically modified tissue might be less recognizable by proteolytic enzymes; and The crosslinking and modification are preferably stable to achieve optimum long-term results.

The extent of enzymatically catalyzed breakdown of fibrous collagen may be influenced by two factors: the availability to the enzyme of recognizable cleavage sites, and the extent of the helical integrity of the collagen. Previous works have suggested that tissue subjected to fixation and having greater crosslinking density will have a greater resistance to degradation.

Fixation refers to the deactivation of the amino acid of a collagen by reaction with a chemical to minimize the antigenicity of the heterologous biological material and the possibility of enzymatic degradation by collagenase and other proteases. Thus, fixation would enhance the durability of the collagen.

Two types of fixation treatment can be differentiated. The first type is crosslinking, in which one molecule of a fixation agent having multiple functional groups reacts with two or more groups in a collagen. After crosslinking, the mechanical properties of the tissue change. The second type of fixation treatment can be referred to as branching, in which the fixative reacts with a single group only, resulting in a branch produced by the reacted amino acid. In branching, the mechanical properties (e.g., flexibility) of the tissue will normally experience little change.

Both cross-linking and branching will alter the antigenicity of the collagenous tissue if there is modification of a sufficient amount of amino acids, and if the grafting structure (i.e., branching) is large enough to change the local molecular conformation (i.e., both sequential and conformatial antigen determination sites/epitopes). A higher degree of fixation of the fixed biomaterial (tissue) will generally result in lower antigenicity.

Since the host cellular and enzymatic activity is highly associated with inflammation, and the toxicity of the residual fixative may contribute to the local chronic inflamation, a minimal residual toxicity of the prosthesis is desirable. Collagenous tissue for blood-contacting applications, such as for heart valves and conduits, should also have excellent hemocompatibility. Hydrophilicity, charge, surface texture and other surface characteristics on the blood-contacting surface can significantly impact the performance and durability of the tissue when used in these applications. Some trends can be observed in relation to surface tension and hemocompatibility/bioadhesion. R. R. Baier and V. A. DePalma, "The Relation of the Internal Surface of Grafts to Thrombosis", *Management of Arterial Occlusive Disease,* Year Book Medical Publisher, Chicago, Ill., 147–163 (1971) has accumulated an extensive amount of data over many years on the observed trend of biological reactivity of materials as a function of their relative critical surface tensions. An empirically derived graph from their work is divided into three zones: (1) A first zone, coincident to a minimum in biological interaction, is the "hypothetical zone of biocompatability:, which surface tension ranges from 20 to 30 dynes/cm (hydrophobic surface). This zone is the range of surface tensions that most natural arteries possess and is descriptive of relatively nonthrombogenic surfaces. (2) A second zone which ranges from 33 to 38 dynes/cm and comprises the surface tensions of most commonly available polymers, which surprisingly, excludes the most commonly used polymers for vascular grafts (i.e., ePTFE and Dacron). (3) A third zone which ranges from 40 to 72 dynes/cm and known as the zone of "good bioadhesion". This "good bioadhesion" zone would be favored by prostheses in which good ingrowth is required, such as orthopedic and dental implants.

Critical surface tensions in the range of 20 to 30 dynes/cm, which correlate to surfaces dominant with methyl ($CH_3$)

groups, do indicate inherent thromboresistance for implanted specimens.

Biological tissues can be chemically modified or fixed with formaldehyde (FA) or glutaraldehyde (GA). Heterologous and homologous tissues have been fixed and implanted as prostheses for over the past thirty years. Clinically, GA has been the most common fixative. GA modifies most lysyl ε-amino groups, forms cross-linkage between nearby structures, and it polymerizes and gains stability through Schiff base interaction. GA provides adequate modification to minimize the antigenicity of the prosthesis while making the prosthesis hydrophobic and negatively-charged on the surface for good blood interaction. However, the tendencies of GA to markedly alter tissue stiffness and promote tissue calcification are well-known drawbacks of this fixative. For these reasons, GA has been linked to a number of prosthesis failures.

Attempts have been made to reduce the potential for calcification in prostheses that have been fixed with GA. For example, U.S. Pat. No. 5,080,670 to Imamura et al. discloses a number of polyglycidl ethers (sold under the trademark DENACOL by Nagasi Chemicals, Osaka, Japan) for cross-linking tissue heart valves. Imamura et al. believe that the existence of the ether linkage (C—O) in the backbone of the fixative will allow the oxygen arm to work as a flexible joint in the cross-linking bridge, so that the cross-linked tissue can be more flexible and hydrophilic. Biological tissues cross-linked with polyglycidl ethers have shown great flexibility (pliability) and resistance to calcification when compared with GA fixation as used with tissue heart valves. Further, the epoxy compound is less cytotoxic than GA solutions.

Unfortunately, hydrophilic material has a tendency for water to attach thereto. In addition, more protein and cellular activation has been observed on such hydrophilic surfaces. These interactions may affect or reduce hemocompatibility of the biological tissue.

Another possible drawback with Imamura et al.'s approach is that ether linkages may be highly susceptible to oxidation and thereby lose their cross-linkage within a matter of days after in vivo implantation, especially under stress. See M. A. Schubert, M. J. Wiggins, M. P. Schaefer, A. Hiltner, and J. M. Anderson, "Oxidative Biodegradation Mechanisms of Biaxially Strained Poly(etherurethane urea) Elastomers", J. Biomed. Mater. Res., Vol. 29, 337–347 (1995) ("Schubert et al.").

After implantation of a foreign biological tissue into a human host, macrophages adhere to the implanted or foreign surface, become activated, and can form foreign-body giant cells. These phagocytic cells release superoxide anions, hydrogen peroxide, hypochlorite and hydrolytic enzymes. Local concentrations of these by-products can be quite high. Further, the interfacial environment (i.e., surrounding the implant) changes into the acidic (i.e., lower pH) range. Absorption of α2-macroglobulin has also been observed to play an important role in the biodegradation that results in oxidation and the loss of cross-linkage.

The breakdown of the ether linkage can be clearly observed. A possible explanation for this breakdown will now be posited for this observed degradation (i.e., breakdown). The appearance of new bands in the infrared spectra of explanted hydrophobic polyether tissue samples might be explained by assuming a mechanism similar to that proposed by Wu et al. for the in vivo degradation of poly(ether urethane)s with poly(THF) as the soft segment and/or by assuming a mechanism for the autoxidation of polyethers. Y. Wu, C. Sellitti, J. M. Anderson, A. Hiltner, G. A. Lodoen and C. R. Payet, "An FTIR-ATR Investigation of In Vivo Poly(ether urethane) Degradation", J. Appl. Polym. Sci., Vol. 46, 201–211 (1992). Wu et al. reported that superoxide anion radicals combine rapidly with protons to form hydroperoxide radicals HOO., which attack the polymer backbone leading to the hydroperoxide groups POOH. The hydroperoxide subsequently dehydrates to form an ester, which will then hydrolyze due to esterases, leading to chain scission and resulting in the formation of carboxylic acid and alcohol groups. This is illustrated on the left side of the chain in FIG. 1.

Schubert et al. suggest that the radicals P. of might be formed by hydrogen abstraction from the polyether soft segment by thiyl radicals that formed after the reaction of hydroxy radicals with free thiol groups of (absorbed) α2-macroglobulin. This is illustrated on the right side of the chain in FIG. 1.

Another form of degradation (autoxidation) can take place by way of a variety of reaction paths, all involving radical mechanisms. In short, the propagation reactions of this autoxidation consist of the formation and decomposition of hydroperoxide groups on the polymer backbone. Homolysis of the hydroperoxide leads to hydroxyl and alcoxy radicals (PO.). The latter can form an ester by hydrogen fragmentation or can lead to chain scission, resulting in the formation of aldehyde and ester groups. These reactions occur without the loss of radical activity, and the remaining radicals can continue the dehydration. Hydrolysis of the ester bonds will lead to the formation of alcohol and acid groups.

Once the cross-linkage formed by polyglycidl ether is cleaved at its ester linkage, modification to the tissue will be the same regardless of whether it is a mono- or poly-epoxide, and regardless of the type of polyglycidl ether used. The structure at the modification site is always either:

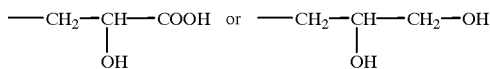

From previous studies, it is observed that mono-functional glycidyl ethers cannot block the recognition of enzyme and possible antigenicity. As observed with fresh tissue, methyl glycidyl ether (DENACOL EX-131) fixed tissue disintegrated into pieces with bacterial collagenase when the test tube was shaken. See R. Tu, S. H. Shen, D. Lin, C. Hata, K. Thyagarajan, Y. Noishiki and R. J. Quijano, "Fixation of Bioprosthetic Tissues With Monofunctional and Multifunctional Polyepoxy Compounds", J. Biomed. Mater. Res., Vol. 28, 677–684 (1994). In addition, the increment in its free amino group content due to the cleavage of peptide bonds was comparable to that seen in the fresh tissue. In other words, the glycidyl ether was not effective in effecting cross-linkage.

The above strongly suggests that the glycidyl ether is highly susceptible to oxidation at its ether linkage. Distintegrated linkage failed to protect the recognition of collagenase. Thus, the glycidyl ether did not provide the desired results.

Thus, there still remains a need for a tissue fixation method and treatment which minimizes calcification while avoiding the problems experienced by the known methods and treatments described above.

SUMMARY OF THE DISCLOSURE

It is an object of the present invention to provide a stable epoxide tissue treatment agent for collagenous tissue modification that reduces the possibility of oxidation enzymatic attack and antigenicity.

In order to accomplish the objects of the present invention, the present invention provides an epoxy compound that has a hydrocarbon backbone, that is water-soluble, and which does not contain an ether or ester linkage in its backbone. Examples of suitable epoxide agents include mono- or diepoxides that have the following basic formulas:

Monoepoxide:

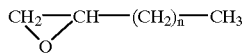

Diepoxide:

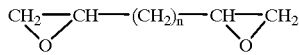

where n=1 to 10.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices, compositions, components, mechanisms and methods are omitted so as to not obscure the description of the present invention with unnecessary detail.

For purposes of the present invention, the term "collagenous tissue" refers to material which may be derived from different animals, such as mammals. Specific examples include, but are not limited to, porcine heart valves; bovine pericardium; connective tissue derived materials such as dura mater, tendons, ligaments, skin patches; arteries; veins; and the like.

The present invention provides a cross-linking agent for use in tissue fixation of collagenous material. The agent is an epoxy compound that has a hydrocarbon backbone, that is water-soluble and which does not contain an ether or ester linkage in its backbone. Examples of suitable epoxide agents include mono- or diepoxides that have the following basic formulas:

Monoepoxide:

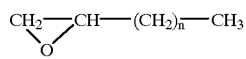

Diepoxide:

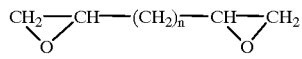

where n=1 to 10. For example, a monoepoxide where n is equal to 3 is as follows:

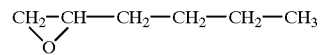

Monoepoxides according to the present invention are generally used to modify tissue where a greater flexibility is important. Examples of such tissues include venous valves, esophagus and ureters. Polyepoxides (i.e., diepoxides and epoxides having two or more reactive epoxide groups) according to the present invention are generally used to modify tissue which may be used in applications where significant stress and load are experienced after implantation. Examples of such tissues include heart valves in arterial systems, ligaments and tendons.

Figure 1:
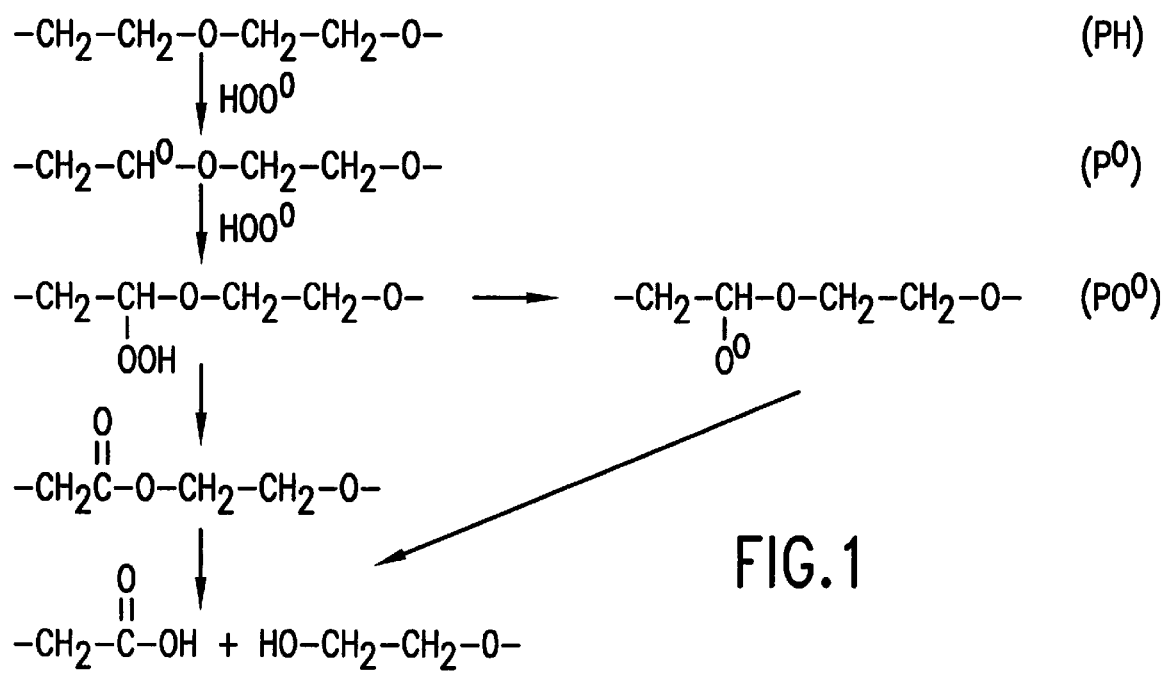
FIG. 1 illustrates proposed mechanisms for the in vivo degradation of polyethylene oxide.
Figure 2:
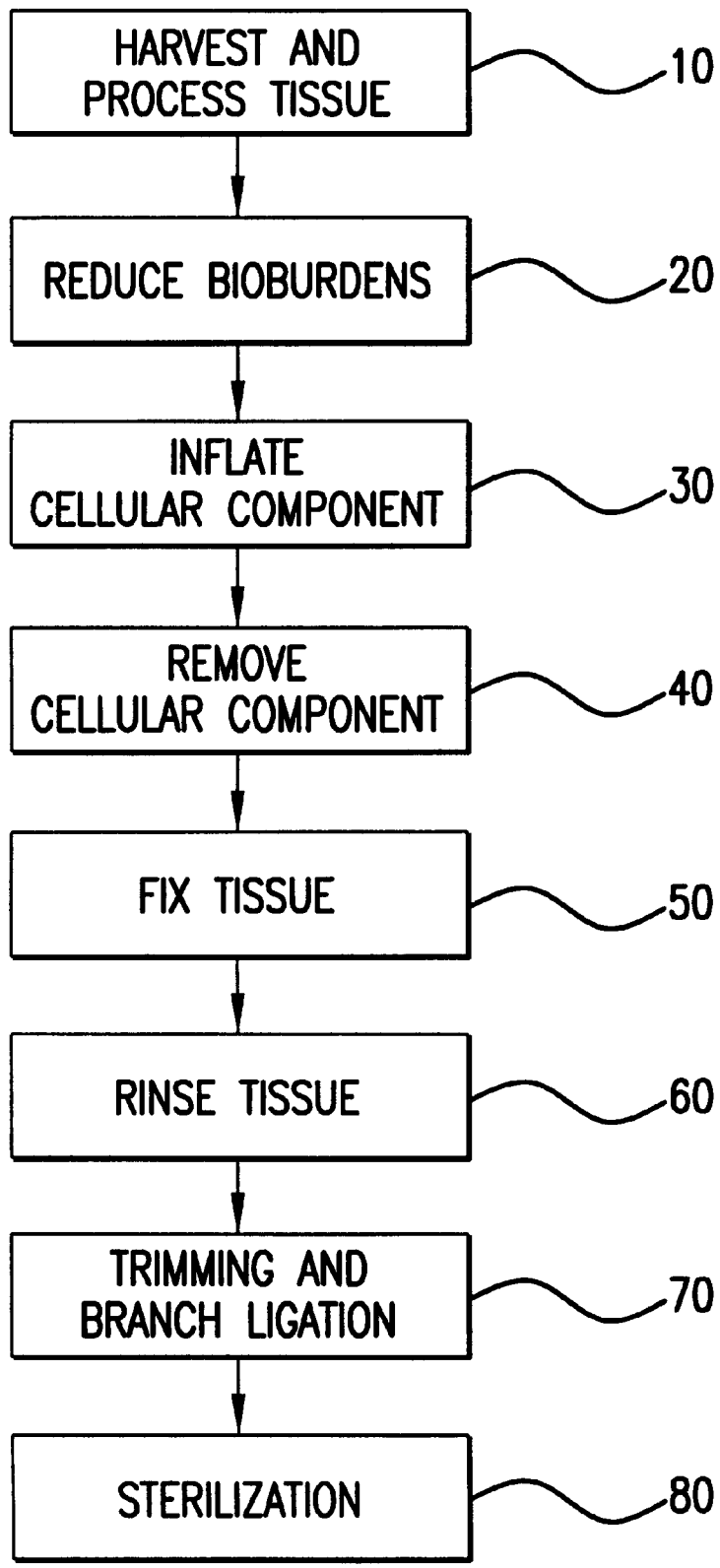
FIG. 2 is a flowchart illustrating a method for producing a bioprosthesis according to the present invention.

The cross-linking agent of the present invention can be used to fix or modify a wide variety of bioprosthetic tissues, including bovine pericardium and porcine aortic valves. The method of treating and preparing the bioprosthetic tissue is summarized in the flowchart of FIG. 2, and is set forth as follows.

In step 10, a collagenous tissue is harvested and processed. A suitable collagenous tissue, such as an artery or vein, is harvested from a mammal, and excess muscle, fat and connective tissues are trimmed according to known methods. The collagenous tissue is cleaned and prepared in accordance with known methods. The blood vessel is washed inside and out with cold saline solution to remove any remaining blood.

In step 20, bioburden levels are reduced by immersing each tissue in 70% ethanol for about one hour. The tissues are then stored in 30% ethanol for any desired period of time.

In step 30, the cellular component is inflated. This can be done by injecting the lumen of each tissue vessel with fresh filtered water and then transferring them to a container of fresh filtered water. The tissue is then kept refrigerated for at least one hour while in the fresh filtered water prior to sonication.

In step 40, the tissue is sonicated in filtered water for a period of time sufficient to remove the cellular component. It is desirable to remove the cellular component because it has greater antigenicity. The tissue is then thoroughly washed with water.

In step 50, fixation is performed. The previously prepared collagenous tissue is immersed in an aqueous solution of the water-soluble epoxide cross-linking agent of the present invention at a pH of 8.5 to 10.5 for a time (e.g., 1 to 30 days) sufficient to permit irreversible cross-linking. The concentration of the epoxide crosslinking agent preferably ranges from 0.01 M to 1.0 M, and more preferably, is between 0.05 M to 0.5 M. The fixation solution is changed every two to three days.

In step 60, the collagenous tissue is removed from the fixation solution and is rinsed with a suitable rinsing solution such as phosphate buffered saline, with or without amino acid. This rinsing removes residual fixative reactivity.

In step 70, final trimming and branch ligation are performed. Excess connective tissue is carefully trimmed away without damaging the vessel branches. Any tissue vessel having holes, avulsed branches, blood stains or other visual structural defects will not be used. All branches are suture-ligated using 4-0 or 5-0 Prolene suture.

In step 80, final sterilization is performed. The collagenous tissue is sterilized with a non-aldehyde sterilant, such as 0.1% iodine solution, and then stored in 30% ethanol solution until the tissue is to be implanted.

FIRST EXAMPLE
Cross-Linking Arterial Graft with Diepoxides

A fresh bioprosthetic tissue, such as a bovine artery, is incubated in an aqueous solution of a water-soluble polyepoxide cross-linking agent. More specifically, a 1,2,7,8-diepoxyoctane at 0.2 M is buffered to a pH of 9.5 with carbonate-bicarbonate buffer with 5% ethanol. The artery is exposed to the solution for 14 days at room temperature (e.g., 25 degrees Celcius) to permit irreversible cross-linking. The fixation solution is changed every three days.

SECOND EXAMPLE
Modification of Venous Conduit with Valve

A vein conduit having venous valves is incubated in an aqueous solution of a water-soluble polyepoxide cross-linking agent. More specifically, a 1,2-epoxyoctane at 0.2 M is buffered to a pH of 9.5 with carbonate-bicarbonate buffer with 10% ethanol. The vein is exposed to the solution for 14 days at 25 degrees Celcius to permit complete modification.

What is claimed is:

1. A bioprosthetic tissue containing a cross-linked epoxy compound having a hydrocarbon backbone, said epoxy compound being water-soluble and whose backbone is devoid of either an ether or ester linkage.

2. The bioprosthetic tissue of claim 1, wherein the epoxy compound is a monoepoxide having the following basic formula:

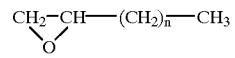

where n=1 to 10.

3. The bioprosthetic tissue of claim 1, wherein the epoxy compound is a polyepoxide having the following basic formula:

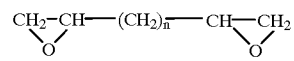

where n=1 to 10.

4. The bioprosthetic tissue of claim 1, wherein the epoxy compound is a 1,2,7,8-diepoxyoctane.

5. The bioprosthetic tissue of claim 1, wherein the epoxy compound is a 1,2-epoxyoctane.

6. The bioprosthetic tissue of claim 1, wherein the tissue is selected from the group consisting of porcine aortic valves, bovine pericardium, dura mater, tendons, ligaments, skin patches, arteries, and veins.

* * * * *